United States Patent
Prinsen et al.

(10) Patent No.: US 9,406,128 B2
(45) Date of Patent: Aug. 2, 2016

(54) X-RAY DOSE DISTRIBUTION CALCULATION FOR A COMPUTED TOMOGRAPHY EXAMINATION

(71) Applicant: KONINKLIJKE PHILIPS N.V., Eindhoven (NL)

(72) Inventors: Peter Prinsen, Eindhoven (NL); Jens Wiegert, Aachen (DE); Cristian Lorenz, Hamburg (DE); Heike Ruppertshofen, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/766,142

(22) PCT Filed: Apr. 21, 2014

(86) PCT No.: PCT/EP2014/058031
§ 371 (c)(1),
(2) Date: Aug. 6, 2015

(87) PCT Pub. No.: WO2014/173851
PCT Pub. Date: Oct. 30, 2014

(65) Prior Publication Data
US 2016/0035086 A1   Feb. 4, 2016

(30) Foreign Application Priority Data

Apr. 24, 2013   (EP) ..................................... 13165164

(51) Int. Cl.
*G06K 9/00*   (2006.01)
*G06T 7/00*   (2006.01)
(Continued)

(52) U.S. Cl.
CPC ................ *G06T 7/0012* (2013.01); *A61B 6/03* (2013.01); *A61B 6/032* (2013.01); *A61B 6/5294* (2013.01);
(Continued)

(58) Field of Classification Search
None
See application file for complete search history.

(56) References Cited

U.S. PATENT DOCUMENTS

| 4,455,609 A | 6/1984 | Inamura et al. |
| 5,418,715 A | 5/1995 | Deasy |

(Continued)

FOREIGN PATENT DOCUMENTS

| EP | 1943951 A1 | 7/2008 |
| EP | 2465435 A1 | 6/2012 |

(Continued)

OTHER PUBLICATIONS

Freud, N., et al.; A Hybrid Approach for Fast Simulation of Dose Deposition in Stereotactic Synchrotron Radiotherapy; 2008; IEEE Trans. on Nuclear Science; 55(3)1008-1017.

(Continued)

*Primary Examiner* — Aaron W Carter (57) ABSTRACT

The invention relates to an apparatus (18) for calculating an x-ray dose distribution within an object for a computed tomography examination. A primary flux determination unit (15) determines firstly a primary flux distribution within the object, wherein then this determined primary flux distribution is used as an initial total flux distribution by a total flux determination unit (16) while applying a six-flux model algorithm. This allows the determination of the total flux distribution to start with a relatively good first approximation of the total flux distribution such that the six-flux model algorithm can determine the total flux distribution very fast. The determined total flux distribution is finally used by a dose distribution determination unit (17) for determining a total dose distribution. The apparatus allows therefore for a very fast determination of x-ray dose distributions for computed tomography examinations.

15 Claims, 4 Drawing Sheets

(51) Int. Cl.
*A61B 6/03* (2006.01)
*A61B 6/00* (2006.01)
*G06T 11/00* (2006.01)
*G06T 17/00* (2006.01)
*A61N 5/10* (2006.01)

(52) U.S. Cl.
CPC ............... *A61B 6/542* (2013.01); *G06T 11/003* (2013.01); *G06T 17/00* (2013.01); *A61N 2005/1034* (2013.01); *G06T 2207/10072* (2013.01)

(56) References Cited

U.S. PATENT DOCUMENTS

| | | | |
|---|---|---|---|
| 7,782,996 B2* | 8/2010 | Ruhrnschopf | A61B 6/032 378/4 |
| 8,238,513 B2* | 8/2012 | Ma | A61B 6/032 378/6 |
| 9,140,803 B2* | 9/2015 | Bertram | A61B 6/032 |
| 9,295,432 B2* | 3/2016 | Gerland | A61B 6/037 |
| 2005/0143965 A1 | 6/2005 | Failla et al. | |
| 2006/0259282 A1 | 11/2006 | Failla et al. | |
| 2008/0091388 A1 | 4/2008 | Failla et al. | |
| 2008/0292055 A1 | 11/2008 | Boone | |
| 2010/0119139 A1* | 5/2010 | Bertram | G06T 11/005 382/131 |
| 2010/0208964 A1* | 8/2010 | Wiegert | G06T 11/005 382/131 |
| 2010/0310037 A1* | 12/2010 | Wang | A61B 6/032 378/6 |
| 2011/0044524 A1* | 2/2011 | Wang | G01R 33/54 382/131 |
| 2011/0110573 A1* | 5/2011 | Wiegert | A61B 6/032 382/131 |
| 2012/0230470 A1 | 9/2012 | Bertram et al. | |
| 2013/0158879 A1* | 6/2013 | Hu | A61N 5/1031 702/19 |
| 2013/0259344 A1* | 10/2013 | Petersilka | G06T 11/006 382/131 |
| 2013/0329982 A1* | 12/2013 | Alghamdi | G06F 19/3437 382/132 |
| 2014/0263990 A1* | 9/2014 | Kawrykow | A61N 5/1031 250/252.1 |
| 2015/0265224 A1* | 9/2015 | Gerland | A61B 6/032 382/131 |

FOREIGN PATENT DOCUMENTS

| | | |
|---|---|---|
| WO | 2007062178 A2 | 5/2007 |
| WO | 2012075577 A1 | 6/2012 |
| WO | 2014060913 A1 | 4/2014 |

OTHER PUBLICATIONS

Geleijns, J., et al.; Radiation Exposure to Patients in a Multicenter Coronary Angiography Trial (CORE 64); 2011; Medical Physics and Informatics; 196(5)1126-1132.

Lathrop, K. D.; Remedies for Ray Effects; 1971; Nuclear Science and Engineering; 45(3), Abstract Only.

Sasse, C., et al.; Evaluation of an improved hybrid six-flux/zone model for radiative transfer in rectangular enclosures; 1995; International Journal of Heat and Mass Transfer; 38(18), Abstract Only.

Smekens, F., et al.; Simulation of dose deposition in stereotactic synchrotron radiation therapy: a fast approach combining Monte Carlo and deterministic algorithms; 2009; Phys. Med. Biol.; 54(15), Abstract Only.

Zhao, H.; Fast ray-tracing technique to calculate line integral paths in voxel arrays; 2003; IEEE Nuclear Science Symposium Conf. Record; vol. 4; pp., Abstract Only.

\* cited by examiner

X-RAY DOSE DISTRIBUTION CALCULATION FOR A COMPUTED TOMOGRAPHY EXAMINATION

FIELD OF THE INVENTION

The invention relates to an apparatus, a method and a computer program for calculating an x-ray dose distribution within an object for a computed tomography examination. The invention relates further to a computed tomography system comprising the apparatus for calculating the x-ray dose distribution within the object.

BACKGROUND OF THE INVENTION

It is known to use a Monte Carlo method for calculating an x-ray dose distribution within a person during a computed tomography examination, wherein the Monte Carlo method uses x-ray parameters defining x-ray properties like the position, orientation and intensity of x-rays and a model of the person defining the influence on traversing x-rays by the person during the computed tomography examination. A corresponding Monte Carlo method is disclosed, for instance, in the article "Radiation Exposure to Patients in a Multicenter Coronary Angiography Trial (CORE 64)" by J. Geleijns et al., Medical Physics and Informatics, volume 196, number 5, pages 1126 to 1132 (2011). This Monte Carlo based calculation of the x-ray dose distribution within the person for a computed tomography examination requires high computational efforts and takes therefore a relatively long time.

SUMMARY OF THE INVENTION

It is an object of the present invention to provide an apparatus, a method and a computer program for calculating an x-ray dose distribution within an object for a computed tomography examination, which allow for a faster calculation of the x-ray dose distribution. It is a further object of the present invention to provide a computed tomography system comprising the apparatus for calculating the x-ray dose distribution.

In a first aspect of the present invention an apparatus for calculating an x-ray dose distribution within an object for a computed tomography examination is presented, wherein the apparatus comprises:

a model providing unit for providing a model of the object, wherein the model comprises voxels to which x-ray interaction properties are assigned, wherein an x-ray interaction property assigned to a voxel defines an influence of an x-ray traversing an object element of the object, which corresponds to the voxel, by the object element, an x-ray parameters providing unit for providing x-ray parameters defining x-ray properties during the computed tomography examination, a primary flux determination unit for determining a primary flux distribution within the object, which is caused by the computed tomography examination, based on the provided model and the provided x-ray parameters, wherein primary fluxes are determined, which are assigned to surfaces of the voxels, a total flux determination unit for determining a total flux distribution within the object based on an initial total flux distribution, the provided model and the provided x-ray parameters by using a six-flux model algorithm, wherein the initial total flux distribution is defined by the determined primary flux distribution, and a dose distribution determination unit for determining a total dose distribution within the object based on the determined total flux distribution.

Since the primary flux determination unit determines firstly a primary flux distribution within the object, wherein then this determined primary flux distribution is used as an initial total flux distribution by the total flux determination unit while applying the six-flux model algorithm, the determination of the total flux distribution can start with a relatively good first approximation of the total flux distribution such that the six-flux model algorithm can determine the total flux distribution faster. Moreover, since this faster determined total flux distribution is used for determining the total dose distribution, also the total dose distribution can be determined faster.

The provided x-ray parameters define preferentially the acquisition geometry, i.e. the position and orientation of the x-rays relative to the object during the computed tomography examination, the flux and optionally also the energy of the x-rays. The x-ray interaction properties assigned to the voxels define, for instance, the absorption, the scattering, et cetera of an x-ray traversing the respective voxel. The model can be generated by reconstructing a computed tomography image of the object, by segmenting the computed tomography image and by assigning the x-ray interaction properties to the different segments based on a database comprising assignments between the different segments and the x-ray interaction properties. For example, the object can be a living being like a person or an animal and the segments can represent bone, tissue, metal and other possible parts within the living being, wherein, since it is assumed that the x-ray interaction properties of these parts of the living being are known, for instance, stored in a table, the x-ray interaction properties can be assigned to these segments and thus to the voxels of the respective segment.

The model providing unit can be a storing unit, in which the model is stored already and from which the model can be retrieved for providing the same. However, the model providing unit can also be a receiving unit for receiving the model from another device and for providing the received model. The model providing unit can also be adapted to receive a computed tomography image and to generate the model based on the computed tomography image, wherein the model providing unit can be adapted to segment the received computed tomography image and to assign the x-ray interaction properties to the segments for generating the model. The model providing unit can also be adapted to generate the model based on other kinds of images of the object like magnetic resonance images.

Also the x-ray parameters providing unit can be a storing unit for storing the x-ray parameters and for providing the stored x-ray parameters. For instance, the x-ray parameters providing unit can have stored different kinds of computed tomography examinations, i.e. different kinds of computed tomography scans, which are related to different sets of x-ray parameters, wherein one of these computed tomography scans may be selected automatically or by a user via a graphical user interface for selecting the related x-ray parameters. The x-ray parameters providing unit may also just be a receiving unit for receiving the x-ray parameters from another device, for instance, from an input device allowing a user to input the x-ray parameters, wherein in this case the x-ray parameters providing unit is adapted to provide the received x-ray parameters.

The flux is preferentially defined as the rate of flow of x-ray photons per unit area. The primary flux is preferentially the flux caused by photons which have not been scattered, whereas a secondary flux is preferentially the flux caused by scattered photons. The total flux distribution preferentially includes the primary flux and the secondary flux.

It is preferred that the primary flux determination unit is adapted to determine the primary flux distribution within the object based on the provided model and the x-ray parameters by using a ray casting algorithm, wherein virtual rays, which are defined by the provided x-ray parameters, are cast through the model and wherein for different locations within the object primary fluxes are determined based on the provided x-ray parameters and based on x-ray interaction properties assigned to voxels having been traversed before reaching the respective location. Since a ray casting approach is used, the primary flux can be calculated along any ray direction and very fast, thereby further increasing the velocity of calculating the dose distribution within the object.

In a preferred embodiment the x-ray interaction properties are at least partly spectral x-ray interaction properties and the primary flux of the respective cast ray reaching the respective location is a primary flux spectrum, i.e. the attenuation caused by the traversed voxels is a spectral attenuation such that the determined primary flux is a primary flux spectrum. Considering the energy dependence can improve the accuracy of determining the total flux distribution and thus the accuracy of calculating the dose distribution within the person, which is based on the determined total flux distribution.

It is further preferred that the primary flux determination unit is adapted to determine for each voxel a primary flux based on the provided model and the x-ray parameters by using the ray casting algorithm and to decompose for each voxel the determined primary flux by dividing the determined primary flux and by assigning the divided primary fluxes to the surfaces of the respective voxel traversed by a respective cast ray for generating the primary flux distribution. Thus, the primary flux determined for a voxel may be decomposed corresponding to surfaces of the voxel traversed by the respective cast ray. For instance, the primary flux determined for a voxel may be projected on normals of the respective voxel surfaces and the projected primary fluxes may be assigned to the respective voxel surfaces. Moreover, the primary flux determination unit may be adapted to use the ray casting algorithm such that at least one voxel is traversed by several cast rays, wherein for a voxel traversed by several cast rays and for each of these traversing rays a primary flux is determined, and to assign an average of the primary fluxes of the several traversing cast rays to the voxel traversed by the several cast rays. The average can be a weighted average, wherein the weight may depend, for instance, on the size of an intersection area between the respective voxel and the respective cast ray. Furthermore, the primary flux determination unit may be adapted to use the ray casting algorithm such that not all voxels are traversed by a cast ray and to determine a primary flux for a voxel not traversed by a cast ray based on the primary fluxes determined for neighboring voxels traversed by a cast ray. These measures can further improve the quality of the determined primary flux distribution, which can lead to an even faster determination of the total flux distribution.

It is also preferred that the primary flux determination unit is adapted to a) determine the primary flux for a respective voxel and a respective cast ray as a primary flux spectrum depending on the flux spectrum of the respective cast ray reaching the respective voxel, wherein the flux spectrum is determined based on the spectral attenuation caused by other voxels, which have been traversed before reaching the respective voxel, and wherein the spectral attenuation is defined by the x-ray interaction properties assigned to the other voxels, and b) decompose for a respective voxel the determined primary flux spectrum by determining a non-spectral primary flux based on the determined spectral primary flux, by dividing the determined non-spectral primary flux into non-spectral primary fluxes and by assigning the divided non-spectral primary fluxes to the surfaces of the respective voxel traversed by the respective cast ray. Thus, the non-spectral primary flux determined for a voxel may be decomposed corresponding to surfaces of the voxel traversed by the respective cast ray, wherein the non-spectral primary flux may be determined, for example, by averaging the spectral primary flux. The non-spectral primary flux determined for a voxel may be projected on normals of the respective voxel surfaces and the projected non-spectral primary fluxes may be assigned to the respective voxel surfaces. This allows considering the energy-dependence of the flux also during the calculation of the total flux distribution, without increasing the computational efforts for calculating the total flux distribution. Thus, the accuracy of determining the total flux distribution and thus of calculating the dose distribution within the object can be improved, without increasing the computational efforts.

The primary flux determination unit may be adapted to assign the primary flux of a cast ray at the location of a surface of a voxel to the surface, if the cast ray traverses the surface. Thus, for instance, the primary flux for a surface may be directly determined, without necessarily firstly determining the primary flux of a voxel and then decomposing the primary fluxes determined for the voxel. Moreover, the primary flux determination unit may be adapted to use the ray casting algorithm such that a surface of at least one voxel is traversed by several cast rays, wherein for a surface traversed by several cast rays and for each of these traversing rays a primary flux is determined, and to assign an average of the primary fluxes of the several traversing cast rays to the surface traversed by the several cast rays. The average of the primary fluxes of the several traversing cast rays may be a weighted average, wherein the weights may depend on the size of an intersection area between the respective cast ray and the respective surface. Furthermore, the primary flux determination unit may be adapted to use the ray casting algorithm such that not all surfaces are traversed by a cast ray and to determine a primary flux for a surface of a voxel not traversed by a cast ray based on the primary fluxes assigned to neighboring surfaces traversed by a cast ray. These measures can further improve the accuracy of the determined primary flux, which in turn may finally lead to an even faster determination of the total dose distribution.

In a further embodiment the x-ray dose distribution determination unit is adapted to a) subtract the determined primary flux distribution from the determined total flux distribution for determining a secondary flux distribution, b) determine a primary dose distribution by providing for each voxel a primary flux and by calculating the primary dose distribution depending on the primary flux provided for each voxel, c) determine a secondary dose distribution depending on the determined secondary flux distribution, and d) determine the total dose distribution by combining the determined primary and secondary dose distributions. For instance, the primary and secondary dose distributions may just be summed up. In step b) the primary flux for each voxel can be provided by calculating the respective primary flux based on the provided model and the provided x-ray parameters, in particular, by using a ray casting algorithm. However, if the primary flux has already been determined for each voxel for determining the primary flux distribution used in step a), in step b) this determined primary flux can be provided for calculating the primary dose distribution, without calculating the primary flux again in step b). Since the primary dose distribution is determined depending on the primary flux determined for each voxel, i.e., for instance, before decomposing the primary flux distribution and possibly compressing the energy information, the primary dose distribution can be determined with an improved accuracy, which in turn leads to an improved accuracy of the total dose distribution being a combination of the high accuracy primary dose distribution and the secondary dose distribution.

In a further aspect of the present invention a computed tomography system is presented, which comprises the apparatus for calculating an x-ray dose distribution within an object for a computed tomography examination as defined in claim 1.

In a further aspect of the present invention a method for calculating an x-ray dose distribution within an object for a computed tomography examination is presented, wherein the method comprises:

providing a model of the object by a model providing unit, wherein the model comprises voxels to which x-ray interaction properties are assigned, wherein an x-ray interaction property assigned to a voxel defines an influence of an x-ray traversing an object element of the object, which corresponds to the voxel, by the object element, providing x-ray parameters defining x-ray properties during the computed tomography examination by an x-ray parameters providing unit, determining a primary flux distribution within the object, which is caused by the computed tomography examination, based on the provided model and the provided x-ray parameters by a primary flux determination unit, wherein primary fluxes are determined, which are assigned to surfaces of the voxels, determining a total flux distribution within the object based on an initial total flux distribution, the provided model and the provided x-ray parameters by using a six-flux model algorithm by a total flux determination unit, wherein the initial total flux distribution is defined by the determined primary flux distribution, and determining a total dose distribution within the object based on the determined total flux distribution by a dose distribution determination unit.

In a further aspect of the present invention a computer program for calculating an x-ray dose distribution within an object for a computed tomography examination is presented, wherein the computer program comprises program code means for causing an apparatus as defined in claim 1 to carry out the steps of the method as defined in claim 14, when the computer program is run on a computer controlling the apparatus.

It shall be understood that the apparatus of claim 1, the computed tomography system of claim 13, the method of claim 14, and the computer program of claim 15 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
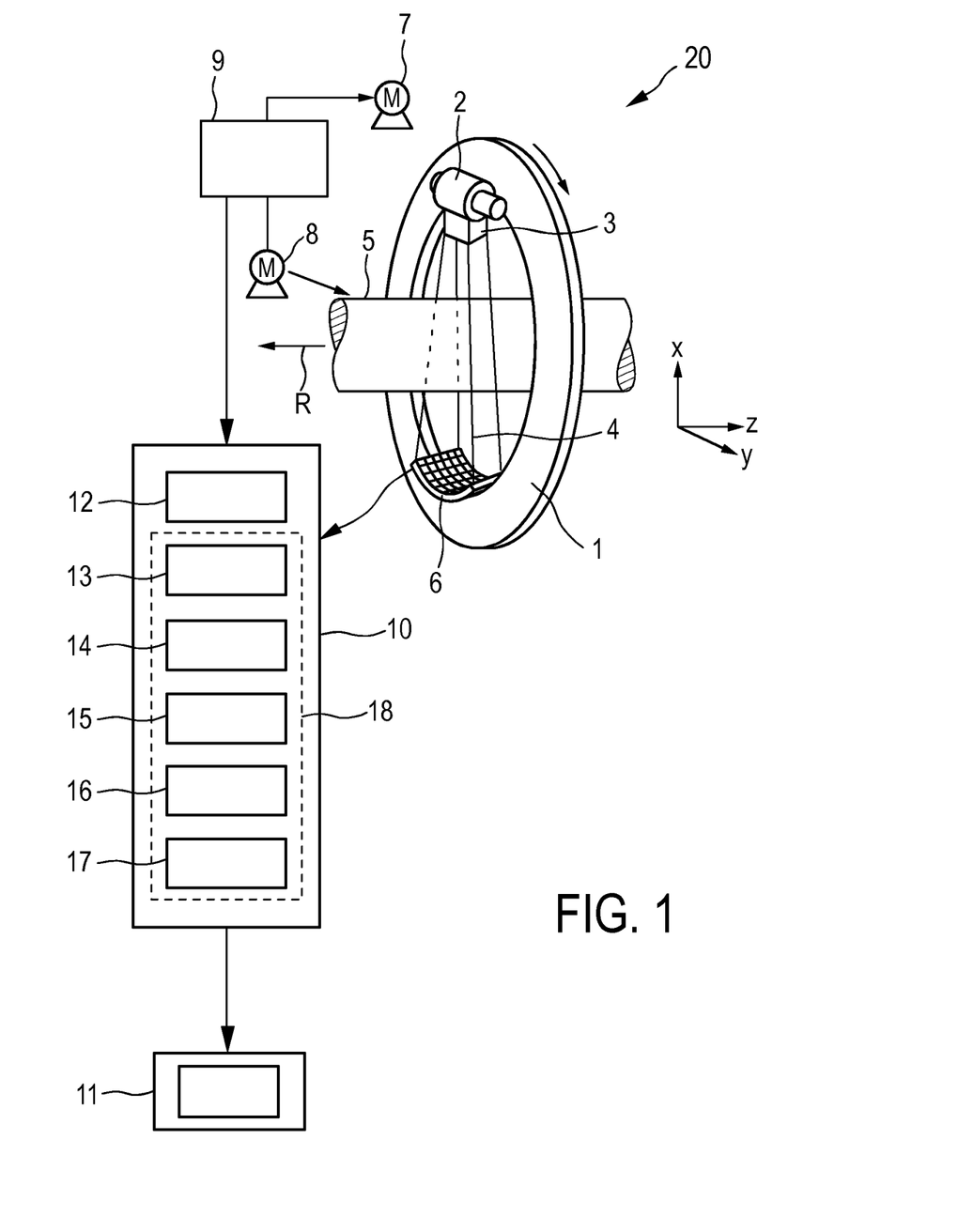
FIG. 1 shows schematically and exemplarily an embodiment of an x-ray computed tomography system, FIGS. 2 and 3 schematically and exemplarily illustrate an example of a decomposition of a primary flux into primary flux components.

FIG. 1 shows schematically and exemplarily an embodiment of a computed tomography system for generating a computed tomography image of an object being, in this embodiment, a person. The computed tomography system 20 includes a gantry 1, which is capable of rotation about a rotational axis R which extends parallel to a z direction. An x-ray tube 2 is mounted on the gantry 1 and provided with a collimator 3, which forms, in this embodiment, a conical radiation beam 4 from the radiation generated by the x-ray tube 2. The radiation traverses the person located within an examination zone 5. After having traversed the examination zone 5 the radiation beam 4 is incident on a detection device 6 comprising a two-dimensional detection surface which is also mounted on the gantry 1.

The computed tomography system 20 comprises two motors 7, 8, wherein the gantry 1 is driven at a preferably constant but adjustable angular speed by the motor 7. The motor 8 is provided for displacing the object arranged on a table in the examination zone 5 parallel to the direction of the rotational axis R or the z axis. These motors 7, 8 are controlled by a control unit 9 such that, for instance, the x-ray tube 2 and the object within the examination zone 5 are moved relatively to each other along a helical trajectory. However, it is also possible that the object is not moved, but that only the x-ray tube 2 is rotated, i.e. that the x-ray tube 2 is moved along a circular trajectory relative to the object within the examination zone 5. Moreover, in another embodiment the collimator 3 can be adapted to form another beam shape like a fan beam and the detection device 6 can comprise a detection surface which is shaped corresponding to the other beam shape, in particular to the fan beam.

During a relative movement of the x-ray tube 2 and the object within the examination zone 5 the detection device 6 generates detection values depending on the radiation incident on the detection surface of the detection device 6. The detection values are projection data which are provided to a reconstruction unit 12 of a processing device 10. The reconstruction unit 12 is adapted to reconstruct a computed tomography image from the received detection values by using known computed tomography reconstruction algorithms like known filtered back projection reconstruction algorithms, Radon inversion reconstruction algorithms, et cetera.

The processing device 10 further comprises an apparatus 18 for calculating an x-ray dose distribution within the object for a computed tomography examination. The apparatus 18 comprises a model providing unit 13 for providing a model of the object, wherein the model comprises voxels to which x-ray interaction properties are assigned. The x-ray interaction properties assigned to a voxel define an influence of an x-ray traversing an object element of the object, which corresponds to the voxel, by the object element. The apparatus 18 further comprises an x-ray parameters providing unit 14 for providing x-ray parameters defining x-ray properties during the computed tomography examination and a primary flux determination unit 15 for determining a primary flux distribution within the object, which is caused by the computed tomography examination, based on the provided model and the provided x-ray parameters, wherein primary fluxes are determined, which are assigned to surfaces of the voxels. The apparatus 18 further comprises a total flux determination unit 16 for determining a total flux distribution within the object by using a six-flux model algorithm determining the total flux distribution based on an initial total flux distribution, the provided model and the provided x-ray parameters, wherein the initial total flux distribution is defined by the determined primary flux distribution. The apparatus 18 also comprises a dose distribution determination unit 17 for determining a total dose distribution within the object based on the determined total flux distribution.

In this embodiment the model providing unit 13 is adapted to segment the reconstructed computed tomography image such that different segments correspond to different parts of the person. The different segmented parts are, for instance, soft tissue, bone, metal, et cetera. The model providing unit 13 comprises a table in which to each part of the person x-ray interaction properties are assigned such that the model can be generated by determining for each voxel to which segmented part it belongs and to assign the corresponding x-ray interaction property to the respective voxel based on the stored table. The x-ray interaction properties assigned to a voxel are, for instance, an absorption coefficient and/or scattering coefficients, which may define the attenuation caused by the respective voxel. Preferentially, after the model has been provided, the total dose distribution within the object can be determined for any x-ray acquisition configuration as defined by the provided x-ray parameters.

The x-ray parameters providing unit 14 is adapted to provide x-ray parameters defining x-ray properties like the position and the orientation of the x-rays, their flux and their energy during the computed tomography examination. The x-ray parameters may be provided depending on a selected computed tomography scan, which may be selected automatically or by a user via a graphical user interface. For interacting with the user the computed tomography system 20 may comprise input means like a keyboard, a computer mouse, a touchpad, et cetera. Moreover, the graphical user interface may be shown on a display 11.

The primary flux determination unit 15 is adapted to determine the primary flux distribution by determining for each voxel a primary flux based on the provided model and the x-ray parameters by using a ray casting algorithm, wherein virtual rays, which are defined by the provided x-ray parameters, are cast through the model and wherein for each voxel traversed by the respective cast virtual ray the primary flux is determined. In this embodiment the primary flux determination unit 15 is adapted to determine the primary flux for a respective voxel and a respective cast ray depending on the flux of the respective ray reaching the respective voxel, wherein the flux is determined based on the attenuation caused by other voxels, which have been traversed before reaching the respective voxel, wherein the attenuation is defined by the x-ray interaction properties assigned to the other voxels and wherein the flux of the respective cast ray reaching the respective voxel is a flux spectrum and the attenuation caused by the other voxels is a spectral attenuation such that the determined primary flux is a primary flux spectrum. Besides through attenuation, the flux may also be reduced due to divergence of the beam. In another embodiment the energy-dependence may not be considered such that the flux of the respective cast ray reaching the respective voxel is a single flux value and the attenuation of the other voxels is not considered as being a spectral attenuation. In this case the determined primary flux is not a primary flux spectrum. Moreover, the primary flux determination unit 15 may be adapted to use the ray casting algorithm such that at least one voxel is traversed by several cast rays and to assign an average of the primary fluxes of the several traversing cast rays to the voxel traversed by the several cast rays. The average is preferentially a weighted average, wherein the weights can be chosen in different ways, for instance, depending on, especially proportional to, the length of the ray through the voxel, the volume corresponding to a crossing of that particular ray through the voxel, or by any other method that gives an approximation of the contribution of that particular ray to the total primary flux in the voxel. Furthermore, the primary flux determination unit 15 may be adapted to use the ray casting algorithm such that not all voxels are traversed by a cast ray and to determine a primary flux for a voxel not traversed by a cast ray based on the primary fluxes determined for neighboring voxels traversed by a cast ray. For instance, primary fluxes determined for one or several neighboring voxels may be assigned to the voxel, which is not traversed by a ray, or an interpolation of these primary fluxes may be assigned to this voxel. The neighboring voxels can be direct neighbors, but they can also include nearby voxels, which are not direct neighbors.

Thus, in an embodiment the primary flux is determined by ray casting. A collection of rays is propagated through the object. Each ray is attenuated during its propagation through the object. The attenuation in a certain voxel preferentially depends on the length of the path of the ray in the voxel and the material properties of the voxel as defined by the x-ray interaction properties assigned to the voxel in the usual way. The ray may be represented by a single flux value that is attenuated, or by a collection of flux values, representing a binned energy spectrum, that are attenuated, each possibly in a different way.

The rays in the collection of rays can be uniformly spaced, but they can also be non-uniformly spaced. In the latter case a ray's flux depends on the solid angle associated with that ray, i.e. in this case the respective flux is also determined in consideration of the solid angle of the respective ray. The solid angles associated to the rays are preferentially chosen such that they cover the whole x-ray beam.

The primary flux determination unit 15 is preferentially adapted to decompose for each voxel the determined primary flux into primary flux components corresponding to surfaces of the respective voxel traversed by the respective cast ray for generating the primary flux distribution. The assignment of a primary flux determined for a voxel to the surfaces of the voxel can be done in different ways. One option is to project the primary flux in a voxel on the normals of the surfaces of the voxel and assign the projected outgoing primary fluxes to the respective surfaces. The total flux determination unit 16 is preferentially adapted to use the six-flux model algorithm with the primary flux distribution as initial condition for determining the total flux distribution based on the provided x-ray parameters and the provided model.

In particular, the primary flux determination unit 15 is adapted to decompose for each voxel the determined primary flux spectrum into non-spectral primary flux components corresponding to surfaces of the respective voxel traversed by the respective cast ray for generating the primary flux distribution, wherein a non-spectral primary flux can be determined based on the determined spectral primary flux, wherein the determined non-spectral primary flux can be divided into non-spectral primary fluxes and the divided non-spectral primary fluxes can be assigned to the surfaces of the respective voxel traversed by the respective cast ray. The non-spectral primary flux can be determined from the spectral primary flux by, for instance, averaging the spectral primary flux. The decomposition of the calculated primary flux is illustrated in FIG. 2.

Figure 2:
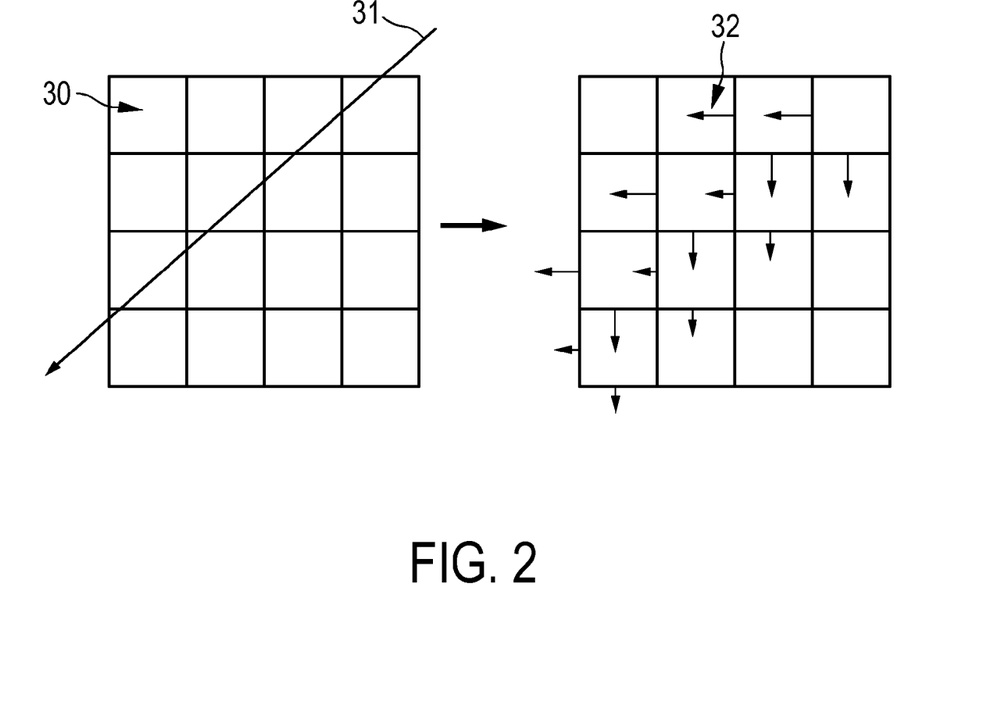

FIG. 2 shows several voxels 30, wherein some of these voxels 30 are traversed by a respective cast ray which is indicated by its center line 31. The decomposed primary flux is indicated by the arrows 32, wherein the lengths of the arrows 32 schematically and exemplarily illustrate the respective primary flux value. The respective length depends on, for instance, the attenuation of the ray when propagating through the model, which leads to a decrease of the primary flux. The length of the respective arrow 32 also depends on the size of the intersection area between the respective voxel and the respective ray and it may depend on the average of the respective flux spectrum. The intersection area is illustrated in FIG. 3.

Figure 3:
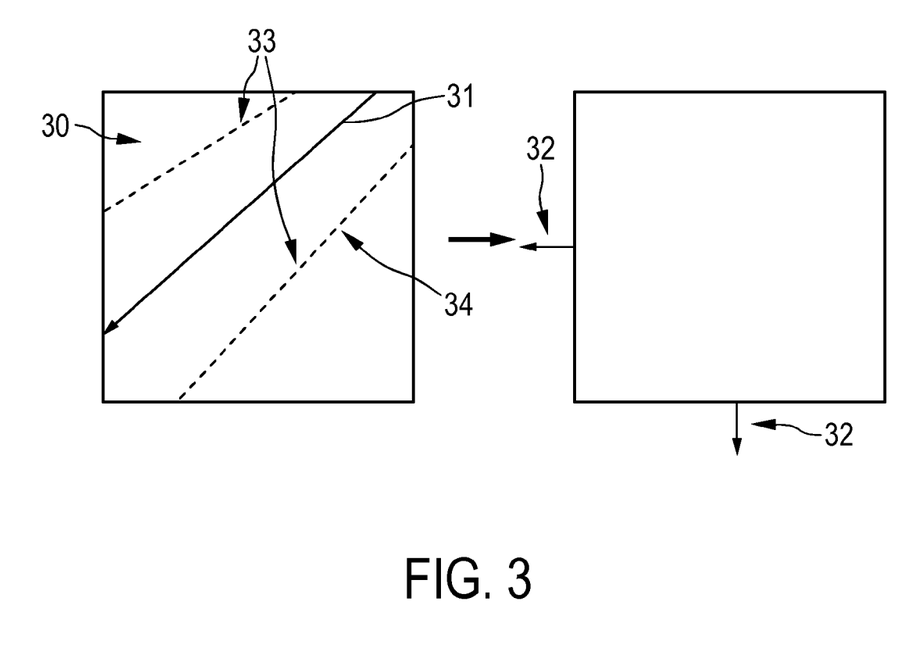

In the left part of FIG. 3 it can be seen that the cast ray 34 with the central line 31 has a certain width exemplarily illustrated by dashed lines 33. The area between the dashed lines 33 is the intersection area. The right part of FIG. 3 shows exemplarily and schematically primary flux components 32 of the model segment 30, i.e. it shows the decomposition of the primary flux into outgoing primary fluxes over the relevant surfaces.

It should be noted that, although in the left part of FIG. 2 only a center line 31 of a cast ray is shown, during the calculation the cast rays have divergent widths as illustrated in the left part of FIG. 3 such that the respective cast ray will generally not only traverse a single surface of a voxel 30 when leaving the respective voxel as it may be deduced from the left part of FIG. 2.

In another embodiment the primary flux of a ray crossing a voxel surface is determined directly through ray casting. A collection of rays as described above may be used and these rays may be attenuated as described above. Whenever a ray crosses the surface of a voxel a primary flux is assigned to that voxel surface. If a single ray crosses a voxel surface, the primary flux of that ray at the voxel surface is assigned to that voxel surface. If multiple rays cross a single voxel surface a weighted average of the primary fluxes of these rays at the voxel surface is assigned to that voxel surface. The weights associated to each primary flux through that particular voxel surface can be chosen in different ways. For example, they can all be chosen equal, they can be chosen proportional to the area of the surface associated with that particular primary flux or they can be chosen by any other method providing a value that gives a proper representation of the contribution of the flux of that ray to the total flux through that particular surface. If the density of rays is not high enough to have at least one ray through every voxel surface that should have a primary flux assigned to it, it is preferentially made sure that the surfaces that did not receive a primary flux value, even though they should have, get one. This can be done in several ways. One is to interpolate between values of neighboring surfaces in the same plane. The other is to assign the primary flux from a ray going through the surface of a voxel also to neighboring surfaces in the same plane. Other ways of distributing primary fluxes locally over nearby voxel surfaces, or interpolating between primary fluxes of nearby rays to determine primary fluxes over voxel surfaces, can be used as well.

Although embodiments have been described above in terms of fluxes, it should be understood that the same calculations can be formulated in terms of intensities, i.e. by considering intensities of rays cast through the provided model, without amending the determination of the flux distributions.

The total flux determination unit 16 is adapted to use a six-flux model algorithm, wherein the decomposed primary fluxes are used as initial condition. In particular, the total flux determination unit 16 may be adapted to use the six-flux model algorithm disclosed in the article "A Fast Six-Flux Radiative Transfer Method for Application in Finite Cloud Models" by K. Gierens et al., Beitraege zur Physik der Atmosphaere, volume 66, number 1-2, pages 73 to 87 (1993), which is herewith incorporated by reference. In this article calculations are described in terms of intensity, which, as already mentioned above, is interchangeable with the term "flux" given the area of a voxel surface. Moreover, in this article the six-flux model gives a relation between the intensity emerging from a voxel through a certain surface and the intensity emerging from neighboring voxels into that voxel (cf., for instance, equation (1) in the above mentioned article by K. Gierens et al.). Based on this relation an iteration equation can be used to find an intensity distribution that obeys this relation everywhere and that is also consistent with the boundary condition of incoming flux from outside the voxelized volume (cf., for instance, equation (3) in the above mentioned article by K. Gierens et al.). Starting from an initial condition, which in this case is the primary flux calculated as described above, it can be iterated, until a stationary solution is reached, which is the total flux.

After the total flux has been determined by using the six-flux model algorithm with the primary flux distribution as initial condition, the dose distribution determination unit 17 can determine the total dose distribution within the object by calculating the amount of energy deposited in the respective voxel, based on the incoming and outgoing fluxes, and then dividing this by the mass of the respective voxel, wherein the mass of the voxel can be provided by the model providing unit 13, particularly as an x-ray interaction property assigned to the respective voxel.

Figure 4:
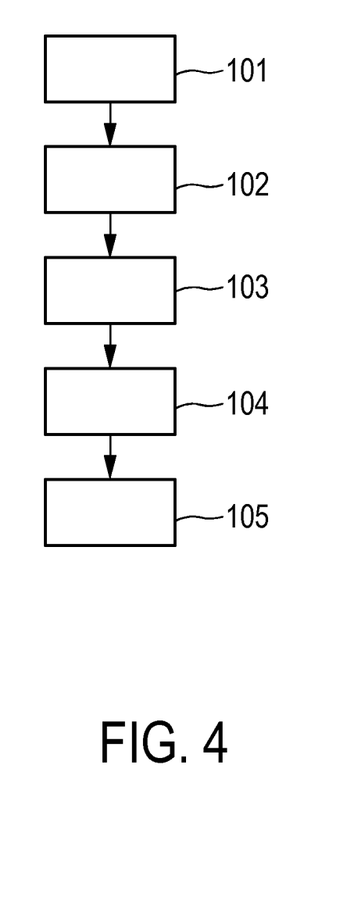
FIG. 4 shows a flowchart exemplarily illustrating an embodiment of a method for calculating an x-ray distribution within an object for a computed tomography examination.

In the following an embodiment of a method for calculating an x-ray dose distribution within an object for a computed tomography examination will exemplarily be described with reference to a flowchart shown in FIG. 4.

In step 101 the model of the object is provided by the model providing unit 13, wherein the model comprises voxels to which x-ray interaction properties are assigned, wherein an x-ray interacting property assigned to a voxel defines an influence of an x-ray traversing an object element of the object, which corresponds to the voxel, by the object element. In step 102 x-ray parameters defining x-ray properties during the computed tomography examination are provided by the x-ray parameters providing unit 14 and in step 103 the primary flux distribution within the object, which is caused by the computed tomography examination, is determined based on the provided model and the provided x-ray parameters by the primary flux determination unit 15. In step 104 the total flux distribution within the object is determined by using the six-flux model algorithm determining the total flux distribution based on an initial total flux distribution, the provided model and the provided x-ray parameters by the total flux determination unit 16, wherein the initial total flux distribution is defined by the determined primary flux distribution. In step 104 the total dose distribution within the object is determined based on the determined total flux distribution by the dose distribution determination unit 17.

Although in an above described embodiment firstly a decomposed primary flux distribution is determined, wherein this decomposed primary flux distribution is used as an initial condition for determining the total flux distribution which is finally used for determining the total dose distribution, in other embodiments the total dose distribution can be determined in another way. For instance, the dose distribution determination unit can be adapted to subtract the determined decomposed primary flux distribution from the determined total flux distribution obtained from the six-flux model algorithm for determining a secondary flux distribution. The dose distribution determination unit can then be adapted to i) determine a primary dose distribution depending on the primary flux distribution, before the primary flux distribution is decomposed and, if spectral primary fluxes are determined, before the spectral primary fluxes are compressed to non-spectral primary fluxes, ii) determine a secondary dose distribution depending on the determined secondary flux distribution and iii) determine the total dose distribution by combining the determined primary and secondary dose distributions. For instance, the primary and secondary dose distributions may just be summed up. Thus, the primary dose in each voxel can also be calculated from the full spectral information before decomposing the primary flux and before compressing the spectral information for determining a primary dose distribution. The decomposed primary flux distribution can then nevertheless be determined and input into the six-flux algorithm for determining a total flux distribution from which the primary flux distribution can be subtracted for determining a secondary flux distribution. The secondary flux distribution can be used for determining a secondary dose distribution, which can be added to the primary dose distribution for calculating the total dose distribution.

If the primary flux distribution is subtracted from the determined total flux distribution for determining a secondary flux distribution, which is then used for determining a secondary dose distribution, and if the determined primary flux distribution before decomposition and before the compression is directly used to determine the primary dose distribution, the primary dose distribution can be calculated more accurately, which in turn leads to an even more accurate total dose distribution being the combination of the determined primary and secondary dose distributions. This direct determination of the primary dose distribution depending on the determined primary flux distribution before decomposition and before the compression without using the six-flux algorithm allows considering any level of energy resolution for the primary beam and any propagation direction, whereas the six-flux algorithm only considers six propagation directions.

In known computed tomography examinations the x-ray dose is often reported as a single computed tomography dose index (CTDI) number. This number is a measure for the dose a standardized phantom would have received in the computed tomography examination. This number does not reflect differences in size between patients and between different sections of the patient, nor does it give any information on dose distribution inside the patient, which is relevant since some parts, particularly organs, are more radiosensitive than others.

In principle, once a computed tomography scan has been performed, a voxelized dose map can be calculated from the voxelized computed tomography image through Monte Carlo calculation, or some other method, since a voxelized attenuation map of the patient is available. However, in practice it is a challenge to produce accurate dose distribution maps within reasonable time. Monte Carlo simulations are currently still very slow. The total flux determination unit is therefore preferentially adapted to use the six-flux algorithm to calculate the radiation flux inside the patient, from which a dose map can then be calculated easily. In the six-flux model the incoming primary flux at the boundary of the patient is calculated after which it is propagated, including scattering, iteratively through the whole patient until a flux equilibrium has been reached.

The apparatus described above with reference to FIG. 1 leads to both, an increase in speed and an improvement of accuracy. The improvement consists of propagating the primary flux through the whole patient, as opposed to, for instance, only to its surface. This can be done fast because one does not keep track of scattered radiation. Moreover, since the determined primary flux is used as an initial condition for the six-flux model algorithm, a good starting distribution is provided for the six-flux model algorithm such that it converges very fast, i.e. less iterations are required for finding an accurate solution.

The apparatus described above with reference to FIG. 1 is adapted to combine a fast primary flux calculation with the six-flux model algorithm, wherein for the primary flux calculation a ray casting approach is used, i.e. the ray casting approach is used to improve the speed and accuracy of a six-flux model based method for calculating dose distribution in computed tomography examinations. This allows considering an energy dependence of the x-rays for determining a primary flux and a propagation of rays in not only six directions, as it would be the case by using a pure six-flux model algorithm without the primary flux distribution defining the initial total flux distribution, which would lead to preferred propagation directions: a problem known as the ray effect as described, for instance, in the article "Remedies for Ray Effects" by K. Lathrop et al., Nuclear Science and Engineering: The Journal of the American Nuclear Society, volume 45, pages 255 to 268 (1971). The consideration of the energy dependence leads to a better achievable accuracy, because attenuation and scattering change the spectrum of the radiation propagating through the patient.

The apparatus is preferentially adapted to firstly calculate the primary flux with a ray casting approach like the ray casting approach described in the articles "Simulation of dose deposition in stereotactic synchrotron radiation therapy: A fast approach combining Monte Carlo and deterministic algorithms" by F. Smekens et al., Physics in Medicine and Biology, volume 54, pages 4671 to 4685 (2009), "Fast Ray-Tracing Technique to Calculate Line Integral Paths in Voxel Arrays" by H. Zhao et al., Nuclear Science Symposium Conference Record, 2003 IEEE, volume 4, pages 2808 to 2812 (2004) or "A Hybrid Approach for Fast Simulation of Dose Deposition in Stereotactic Synchrotron Radiotherapy" by N. Freud et al., IEEE Transactions on Nuclear Science, volume 55, number 3, pages 1008 to 1017 (2008), which are herewith incorporated by reference. However, also another ray casting approach can be used for determining the primary flux distribution. During this calculation of the primary flux any desired energy resolution can be maintained and the respective ray can propagate in any desired direction. During propagation the respective ray is attenuated by tissue of the person, wherein the x-ray interacting properties required for calculating the attenuation are known from the provided model.

In a preferred embodiment during the calculation a ray traversing a voxel has a certain spectral flux and a certain weighting factor which depends on the size of an intersection area, i.e. the volume, between the voxel and the cast ray, for instance, as illustrated in FIG. 4 of the above mentioned article by Freud et al. This primary flux is decomposed into outgoing primary fluxes over the relevant surfaces of the respective voxel and the spectral information is compressed into a single number that is, for example, the average energy of the ray spectrum entering the respective voxel. The contribution of this ray is added to the six outgoing fluxes of the respective voxel. The respective ray then continues along its original path into the next voxel with a modified spectrum due to the attenuation in the current voxel. The primary flux is again decomposed and this continues until the ray leaves the model. This is done for all rays and results in a primary flux distribution within the person. The apparatus may not keep track of incoming fluxes into the voxel, but only of outgoing fluxes, because an incoming flux of a surface of a voxel is equal to an outgoing flux through the bordering surface of the adjacent voxel, except for the boundaries where there are no adjacent voxels and where the incoming flux is also stored in a same way. The primary flux distribution, which may also be regarded as being a primary flux map, is preferentially used as initial condition for the above described six-flux based calculation.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Calculations like the calculation of the primary flux distribution, of the secondary flux distribution, of the primary dose distribution, of the secondary dose distribution, of the total dose distribution, et cetera performed by one or several units or devices can be performed by any other number of units or devices. For example, steps 101 to 105 can be performed by a single unit or by any other number of different units. The calculations and/or the control of the apparatus for calculating an x-ray dose distribution within an object for a computed tomography examination in accordance with the method for calculating the x-ray dose distribution within the object for the computed tomography examination can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an apparatus for calculating an x-ray dose distribution within an object for a computed tomography examination. A primary flux determination unit determines firstly a primary flux distribution within the object, wherein then this determined primary flux distribution is used as an initial total flux distribution by a total flux determination unit while applying a six-flux model algorithm. This allows the determination of the total flux distribution to start with a relatively good first approximation of the total flux distribution such that the six-flux model algorithm can determine the total flux distribution very fast. The determined total flux distribution is finally used by a dose distribution determination unit for determining a total dose distribution. The apparatus allows therefore for a very fast determination of x-ray dose distributions for computed tomography examinations.

The invention claimed is:

1. An apparatus for calculating an x-ray dose distribution within an object for a computed tomography examination, the apparatus comprising:
    a model providing unit for providing a model of the object, wherein the model comprises voxels to which x-ray interaction properties are assigned, wherein an x-ray interaction property assigned to a voxel defines an influence of an x-ray traversing an object element of the object, which corresponds to the voxel, by the object element,
    an x-ray parameters providing unit for providing x-ray parameters defining x-ray properties during the computed tomography examination,
    a primary flux determination unit for determining a primary flux distribution within the object, which is caused by the computed tomography examination, based on the provided model and the provided x-ray parameters, wherein primary fluxes are determined, which are assigned to surfaces of the voxels,
    a total flux determination unit for determining a total flux distribution within the object based on an initial total flux distribution, the provided model and the provided x-ray parameters by using a six-flux model algorithm, wherein the initial total flux distribution is defined by the determined primary flux distribution, and
    a dose distribution determination unit for determining a total dose distribution within the object based on the determined total flux distribution.

2. The apparatus as defined in claim 1, wherein the primary flux determination unit is adapted to determine the primary flux distribution within the object based on the provided model and the x-ray parameters by using a ray casting algorithm, wherein virtual rays, which are defined by the provided x-ray parameters, are cast through the model and wherein for different locations within the object primary fluxes are determined based on the provided x-ray parameters and based on x-ray interaction properties assigned to voxels having been traversed before reaching the respective location.

3. The apparatus as defined in claim 2, wherein the provided x-ray interaction properties are at least partly spectral x-ray interaction properties and the primary flux of the respective cast ray reaching the respective location is a primary flux spectrum.

4. The apparatus as defined in claim 2, wherein the primary flux determination unit is adapted to:
    determine for each voxel a primary flux based on the provided model and the x-ray parameters by using the ray casting algorithm, and
    decompose for each voxel the determined primary flux by dividing the determined primary flux and by assigning the divided primary fluxes to the surfaces of the respective voxel traversed by a respective cast ray for generating the primary flux distribution.

5. The apparatus as defined in claim 4, wherein the primary flux determination unit is adapted to:
    use the ray casting algorithm such that at least one voxel is traversed by several cast rays, wherein for a voxel traversed by several cast rays and for each of these traversing rays a primary flux is determined,
    assign an average of the primary fluxes of the several traversing cast rays to the voxel traversed by the several cast rays.

6. The apparatus as defined in claim 4, wherein the primary flux determination unit is adapted to:
    use the ray casting algorithm such that not all voxels are traversed by a cast ray,
    determine a primary flux for a voxel not traversed by a cast ray based on the primary fluxes determined for neighboring voxels traversed by a cast ray.

7. The apparatus as defined in claim 4, wherein the primary flux determination unit is adapted to:
    determine the primary flux for a respective voxel and a respective cast ray as a primary flux spectrum depending on the flux spectrum of the respective cast ray reaching the respective voxel, wherein the flux spectrum is determined based on the spectral attenuation caused by other voxels, which have been traversed before reaching the respective voxel, and wherein the spectral attenuation is defined by the x-ray interaction properties assigned to the other voxels, decompose for a respective voxel the determined primary flux spectrum by determining a non-spectral primary flux based on the determined spectral primary flux, by dividing the determined non-spectral primary flux into non-spectral primary fluxes and by assigning the divided non-spectral primary fluxes to the surfaces of the respective voxel traversed by the respective cast ray.

8. The apparatus as defined in claim 2, wherein the primary flux determination unit is adapted to assign the primary flux of a cast ray at the location of a surface of a voxel to the surface, if the cast ray traverses the surface.

9. The apparatus as defined in claim 8, wherein the primary flux determination unit adapted to:

use the ray casting algorithm such that a surface of at least one voxel is traversed by several cast rays, wherein for a surface traversed by several cast rays and for each of these traversing rays a primary flux is determined, and assign an average of the primary fluxes of the several traversing cast rays to the surface traversed by the several cast rays.

10. The apparatus as defined in claim 9, wherein the average of the primary fluxes of the several traversing cast rays is a weighted average, wherein the weights depend on the size of an intersection area between the respective cast ray and the respective surface.

11. The apparatus as defined in claim 8, wherein the primary flux determination unit adapted to:

use the ray casting algorithm such that not all surfaces are traversed by a cast ray, and determine a primary flux for a surface of a voxel not traversed by a cast ray based on the primary fluxes assigned to neighboring surfaces traversed by a cast ray.

12. The apparatus as defined in claim 1, wherein the x-ray dose distribution determination unit is adapted to:

subtract the determined primary flux distribution from the determined total flux distribution for determining a secondary flux distribution, determine a primary dose distribution by providing for each voxel a primary flux and by calculating the primary dose distribution depending on the primary flux provided for each voxel, determine a secondary dose distribution depending on the determined secondary flux distribution, and determine the total dose distribution by combining the determined primary and secondary dose distributions.

13. A computed tomography system comprising the apparatus for calculating an x-ray dose distribution within an object for a computed tomography examination as defined in claim 1.

14. A method for calculating an x-ray dose distribution within an object for a computed tomography examination, the method comprising:

providing a model of the object by a model providing unit, wherein the model comprises voxels to which x-ray interaction properties are assigned, wherein an x-ray interaction property assigned to a voxel defines an influence of an x-ray traversing an object element of the object, which corresponds to the voxel, by the object element, providing x-ray parameters defining x-ray properties during the computed tomography examination by an x-ray parameters providing unit, determining a primary flux distribution within the object, which is caused by the computed tomography examination, based on the provided model and the provided x-ray parameters by a primary flux determination unit, wherein primary fluxes are determined, which are assigned to surfaces of the voxels, determining a total flux distribution within the object based on an initial total flux distribution, the provided model and the provided x-ray parameters by using a six-flux model algorithm by a total flux determination unit, wherein the initial total flux distribution is defined by the determined primary flux distribution, and determining a total dose distribution within the object based on the determined total flux distribution by a dose distribution determination unit.

15. A non-transitory computer-readable medium comprising a computer program for calculating an x-ray dose distribution within an object for a computed tomography examination, the computer program comprising program code means for causing an apparatus to carry out the steps of the method as defined in claim 14, when the computer program is run on a computer controlling the apparatus.

\* \* \* \* \*